United States Patent
Kokate et al.

(10) Patent No.: US 6,790,196 B2
(45) Date of Patent: Sep. 14, 2004

(54) ASPIRATING DEVICES FOR REMOVAL OF THROMBUS/LIPID FROM A BODY LUMEN

(75) Inventors: Jaydeep Y. Kokate, Maple Grove, MN (US); Eric M. DoBrava, Crystal, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 60 days.

(21) Appl. No.: 10/025,670

(22) Filed: Dec. 18, 2001

(65) Prior Publication Data

US 2003/0114792 A1 Jun. 19, 2003

(51) Int. Cl.[7] .................................................. A61M 1/00
(52) U.S. Cl. ............................ 604/28; 604/27; 604/35; 604/43; 604/101.03; 604/101.05
(58) Field of Search ...................... 604/101.03, 101.05, 604/27, 28, 35, 43, 96.01

(56) References Cited

U.S. PATENT DOCUMENTS

| | | |
|---|---|---|
| 1,114,268 A | 10/1914 | Kells |
| 1,571,459 A | 2/1926 | Ripley |
| 1,902,418 A | 3/1933 | Pilgrim |
| 2,460,473 A | 2/1949 | Smith |
| 2,564,809 A | 8/1951 | Levene |
| 3,805,787 A | 4/1974 | Banko |
| 3,916,909 A | 11/1975 | Kletschka et al. |
| 3,930,505 A | 1/1976 | Wallach |
| 4,024,866 A | 5/1977 | Wallach |
| 4,061,146 A | 12/1977 | Baehr et al. |
| 4,328,811 A | 5/1982 | Fogarty |
| 4,468,216 A | 8/1984 | Muto |
| 4,690,672 A | 9/1987 | Veltrup |
| 4,696,667 A | 9/1987 | Masch |
| 4,715,848 A | 12/1987 | Beroza |
| 4,790,813 A | 12/1988 | Kensey |
| 4,842,579 A | 6/1989 | Shiber |
| 4,898,547 A | 2/1990 | Bottoms et al. |
| 4,913,698 A | 4/1990 | Ito et al. |
| 4,921,476 A | 5/1990 | Wuchinich |
| 4,935,006 A | 6/1990 | Hasson |
| 4,941,872 A | 7/1990 | Felix et al. |
| 4,950,238 A | 8/1990 | Sullivan |
| 5,037,431 A | 8/1991 | Summers et al. |
| 5,037,432 A | 8/1991 | Molinari |
| 5,058,570 A | 10/1991 | Idemoto et al. |
| 5,061,255 A | 10/1991 | Greenfeld et al. |

(List continued on next page.)

FOREIGN PATENT DOCUMENTS

| | | |
|---|---|---|
| EP | 0 251 512 | 1/1988 |
| EP | 485133 A | 5/1992 |
| WO | WO 90/05493 | 5/1990 |
| WO | WO 98/39046 | 9/1998 |

*Primary Examiner*—Brian L. Casler
*Assistant Examiner*—Jeremy Thissell
(74) *Attorney, Agent, or Firm*—Fish & Richardson P.C., P.A.

(57) ABSTRACT

Methods and devices for treating vulnerable plaque deposits within a blood vessel, having an inner surface and one or more plaque deposits containing a core material are disclosed. A device in accordance with an exemplary embodiment of the present invention includes an elongate shaft having a proximal end and a distal end, a balloon disposed about the elongate shaft for engaging one or more plaque deposits and extracting the core material therefrom, a first venturi section disposed proximally of the balloon, and a second venturi section disposed distally of the balloon. An exemplary method in accordance with the present invention may include the steps of inserting a distal portion of the catheter into a lumen of the blood vessel, positioning the balloon proximate a plaque deposit, inflating the balloon, creating a first stream of fluid proximally of the balloon, collecting the first stream of fluid proximally of the balloon, creating a second stream of fluid distally of the balloon, and collecting the second stream of fluid distally of the balloon.

12 Claims, 3 Drawing Sheets

U.S. PATENT DOCUMENTS

| | | |
|---|---|---|
| 5,084,013 A | 1/1992 | Takase |
| 5,100,425 A | 3/1992 | Fischell et al. |
| 5,135,482 A | 8/1992 | Neracher |
| 5,135,484 A | 8/1992 | Wright |
| 5,180,387 A | 1/1993 | Ghajar et al. |
| 5,195,955 A | 3/1993 | Don Michael |
| 5,201,723 A | 4/1993 | Quinn |
| 5,242,387 A | 9/1993 | Loughlin |
| 5,250,060 A | 10/1993 | Carbo et al. |
| 5,259,842 A | 11/1993 | Plechinger et al. |
| 5,318,518 A | 6/1994 | Plechinger et al. |
| 5,320,599 A | 6/1994 | Griep et al. |
| 5,370,609 A | 12/1994 | Drasler et al. |
| 5,391,145 A | 2/1995 | Dorsey, III |
| 5,411,509 A | 5/1995 | Hilal |
| 5,453,088 A | 9/1995 | Bouewijn et al. |
| 5,496,267 A | 3/1996 | Drasler et al. |
| 5,536,242 A | 7/1996 | Willard et al. |
| 5,606,968 A * | 3/1997 | Mang .................... 128/207.14 |
| 5,730,717 A | 3/1998 | Gelbfish |
| 5,749,858 A | 5/1998 | Cramer |
| 5,772,674 A | 6/1998 | Nakhjavan |
| 5,785,678 A | 7/1998 | Griep et al. |
| 5,908,403 A * | 6/1999 | Bosma et al. ................. 604/43 |
| 6,096,001 A | 8/2000 | Drasler et al. |
| 6,176,844 B1 | 1/2001 | Lee |
| 6,533,767 B2 * | 3/2003 | Johansson et al. .......... 604/507 |

* cited by examiner

ASPIRATING DEVICES FOR REMOVAL OF THROMBUS/LIPID FROM A BODY LUMEN

FIELD OF THE INVENTION

The present invention relates generally to intravascular catheters. More particularly, the present invention relates to intravascular catheters adapted to treat vulnerable plaque.

BACKGROUND OF THE INVENTION

Therapy modalities for heart disease have traditionally focused on treating blood vessels which have become occluded (blocked) or stenotic (narrowed) by calcified plaque deposits. Blood vessels that have become occluded or stenotic in this manner may interrupt the flow of blood that supplies oxygen to the heart muscle. Occluded or stenotic blood vessels have been traditionally treated with a number of medical procedures including angioplasty and atherectomy. Angioplasty techniques such as percutaneous transluminal angioplasty (PTA) and percutaneous transluminal coronary angioplasty (PTCA) are relatively non-invasive methods of treating restrictions in blood vessels. During these procedures, a balloon catheter is advanced over a guidewire until the balloon is positioned proximate to a restriction in a diseased vessel. The balloon is then inflated and the restriction in the vessel is opened. During an atherectomy procedure, the stenotic lesion is mechanically cut or abraded away from the blood vessel wall using an atherectomy catheter.

Calcified plaque deposits are typically comprised of hard materials. Plaque, however, may also be comprised of soft materials or combinations of soft and hard materials. Soft plaque is typically comprised of deposits of cholesterol and other fats which build up within the blood vessels as a patient ages. The build up of plaque in the blood vessels is sometimes referred to as atherosclerosis, or hardening of the arteries.

Atherosclerosis often begins as a small injury to an artery wall. This injury triggers a cyclic cascade of injury and response, inflammation, and healing, which may ultimately lead to the narrowing of the artery. As the atherosclerotic plaque worsens, inflammatory cells, especially macrophages, collect at the site to isolate the debris of the damaged tissue. The result is a core of lipid, macrophages or foam cells and nectrotic tissue, covered by a fibrous cap of scar tissue. If the fibrous cap becomes weakened or is subjected to excessive stress, it may rupture, depositing the trombogenic contents of the core into the blood stream. If the resulting blood clot is severe enough, it may occlude the artery. If this obstruction persists in a coronary artery, a myocardial infarction may result.

Plaque deposits that are at risk of rupturing are sometimes referred to as vulnerable plaque. Vulnerable plaque typically comprises a core of soft materials covered with a fibrous cap. Many of vulnerable plaque deposits do not limit the flow of blood through the blood vessels. It is now appreciated that vulnerable plaques that do not limit flow may be particularly dangerous because they produce no warning symptoms, and can rupture suddenly causing a heart attack and death. This may occur, for example, when the vulnerable plaque ruptures and a blood clot is formed inside the blood vessel lumen causing a blockage.

SUMMARY OF THE INVENTION

The present invention relates generally to intravascular catheters. One embodiment of the present invention relates to intravascular catheters adapted to treat vulnerable plaque. According to one implementation of the present invention, a catheter for treating a blood vessel having an inner surface and one or more plaque deposits including a core material comprises an elongate shaft having a proximal end and a distal end, a first balloon disposed about a first portion of the elongate shaft for engaging the inner surface of the blood vessel, a second balloon disposed about a second portion of the elongate shaft for engaging the inner surface of the blood vessel, and a first venturi section disposed between the first balloon and the second balloon.

DETAILED DESCRIPTION OF THE INVENTION

The following detailed description should be read with reference to the drawings, in which like elements in different drawings are numbered in like fashion. The drawings, which are not necessarily to scale, depict selected embodiments and are not intended to limit the scope of the invention. In some cases, the drawings may be highly diagrammatic in nature. Examples of constructions, materials, dimensions, and manufacturing processes are provided for various elements. Those skilled in the art will recognize that many of the examples provided have suitable alternatives that may be utilized.

Figure 1:
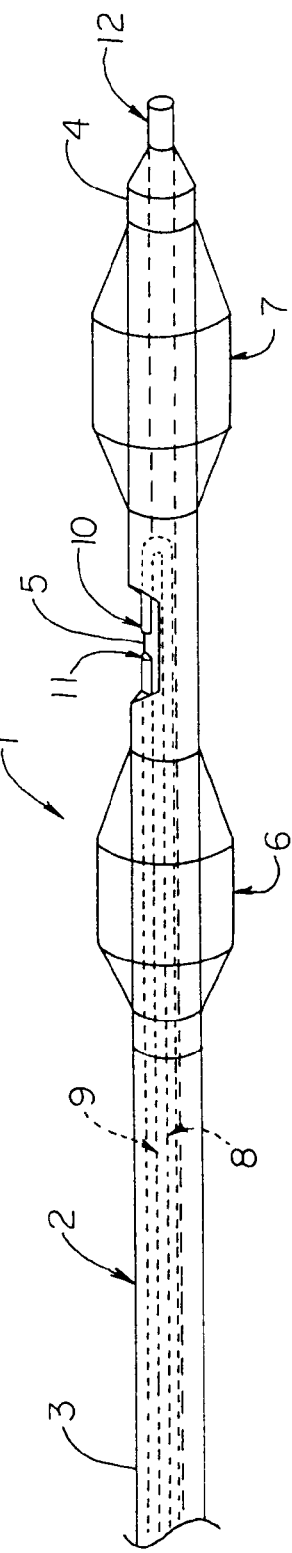
FIG. 1 is a perspective view of a distal portion of the catheter in accordance with an exemplary embodiment of the present invention.

FIG. 1 is a perspective view of a distal portion of a catheter 1 in accordance with the present invention. Catheter 1 includes an elongate shaft 2 having proximal end 3 and distal end 4 which is slideably engaged along delivery sheath 12. A first balloon 6 is disposed about a portion of elongate shaft 2 of catheter 1 proximate first venturi section 5. A second balloon 7 is disposed about a portion of elongate shaft 2 of catheter 1 distal first venturi section 5.

Elongate shaft 2 includes a plurality of walls defining a first tubular member 8 having a first delivery port 10 disposed proximally of balloon 7 and distally of balloon 6. Elongate shaft 2 includes a plurality of walls defining a second tubular member 9 having a first collection port 11 disposed distally of balloon 6 and proximally of first delivery port 10.

Balloons 6 and 7 have an expanded shape, and a contracted shape. Balloons 6 and 7 can be configured such that an engagement surface thereof engages the inner surface of a blood vessel when balloons 6 and 7 assume the expanded shape.

Figure 2:
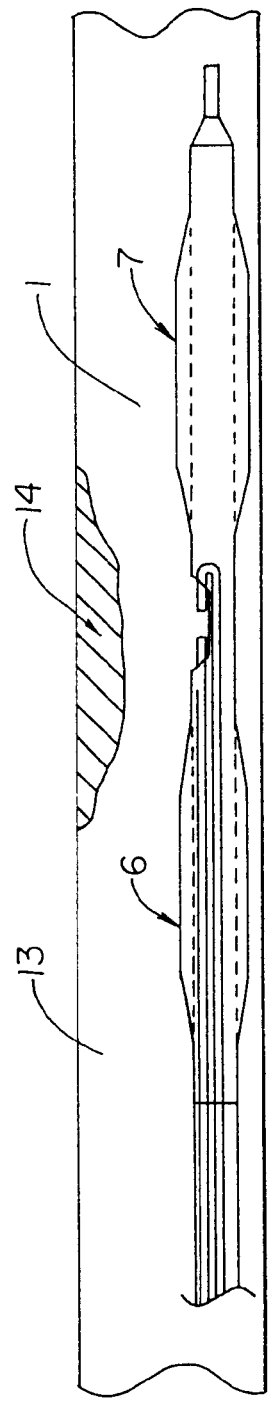
FIG. 2 is a plan view of the distal portion of the catheter in FIG. 1 illustrating one location within the blood vessel where the aspirating device can be used to remove plaque deposits.

FIG. 2 is an additional plan view of the distal portion of catheter 1 illustrated in FIG. 1. In the embodiment of FIG.

1, balloons 6 and 7 are shown having a deflated shape. Also in the embodiment of FIG. 1, distal portion of catheter 1 is disposed within the lumen of a blood vessel 13 containing one or more plaque deposits 14. Catheter 1 is positioned within the lumen of blood vessel 13 such that plaque deposit 14 is located distally of balloon 6 and proximally of balloon 7.

Figure 3:
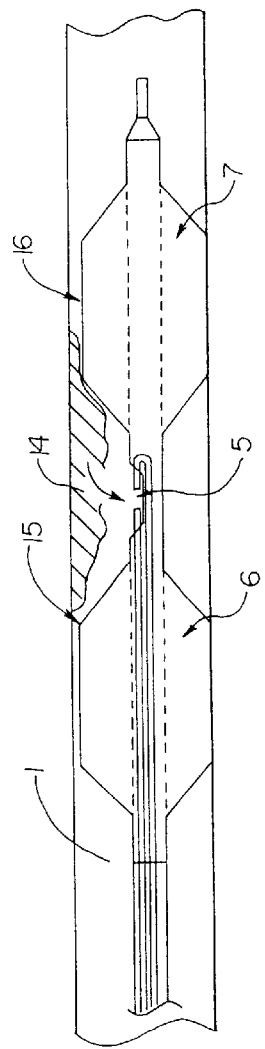
FIG. 3 is a plan view of the distal portion of the catheter in FIG. 1 showing the balloons having an inflated shape engaging the core material from the blood vessel into the venturi section of the catheter.

FIG. 3 is an additional plan view of the distal portion of catheter 1 illustrated in FIG. 1 and FIG. 2. In the embodiment of FIG. 3, balloons 6 and 7 are shown having an expanded shape. In a preferred embodiment, balloon engagement surface 15 and balloon engagement surface 16 are adapted for engaging one or more plaque deposits 14 from the inner wall of the blood vessel. In FIG. 3, arrows are used to illustrate the movement of core material into venturi section 5 as it is extruded from the plaque deposit by the expansion of balloons 6 and 7 and the contact made by balloon engagement surface 15 and balloon engagement surface 16 against plaque deposit 14.

Figure 4:
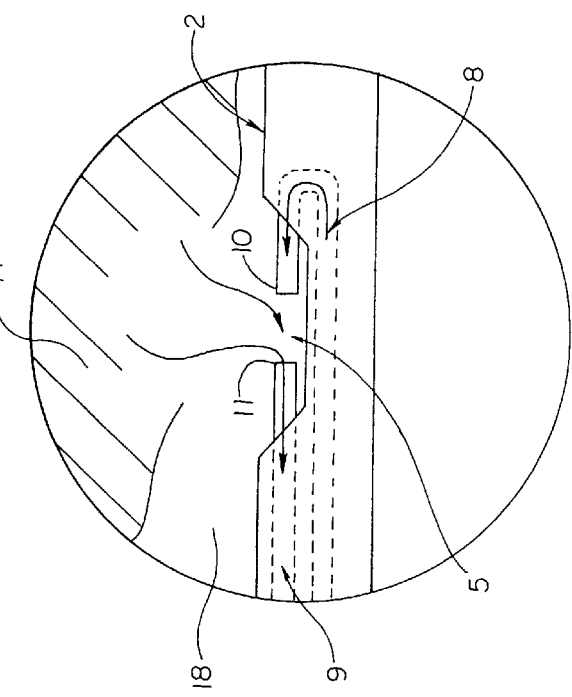
FIG. 4 is an additional plan view of the catheter in FIG. 1 illustrating the flow of plaque deposits from the blood vessel into the venturi section of the catheter.

FIG. 4 is an additional plan view of the distal portion of catheter 1 illustrated in FIGS. 1 through 3. In FIG. 4, arrows are used to illustrate the movement of core material as it is drawn into second tubular member 9 through venturi section 5 and first collection port 11. In some applications, the presence of core material within blood vessel 18 may cause a thrombus to form. When this is the case, the thrombus can be drawn into tubular member 9 through venturi section 5 and first collection port 11.

Figure 5:
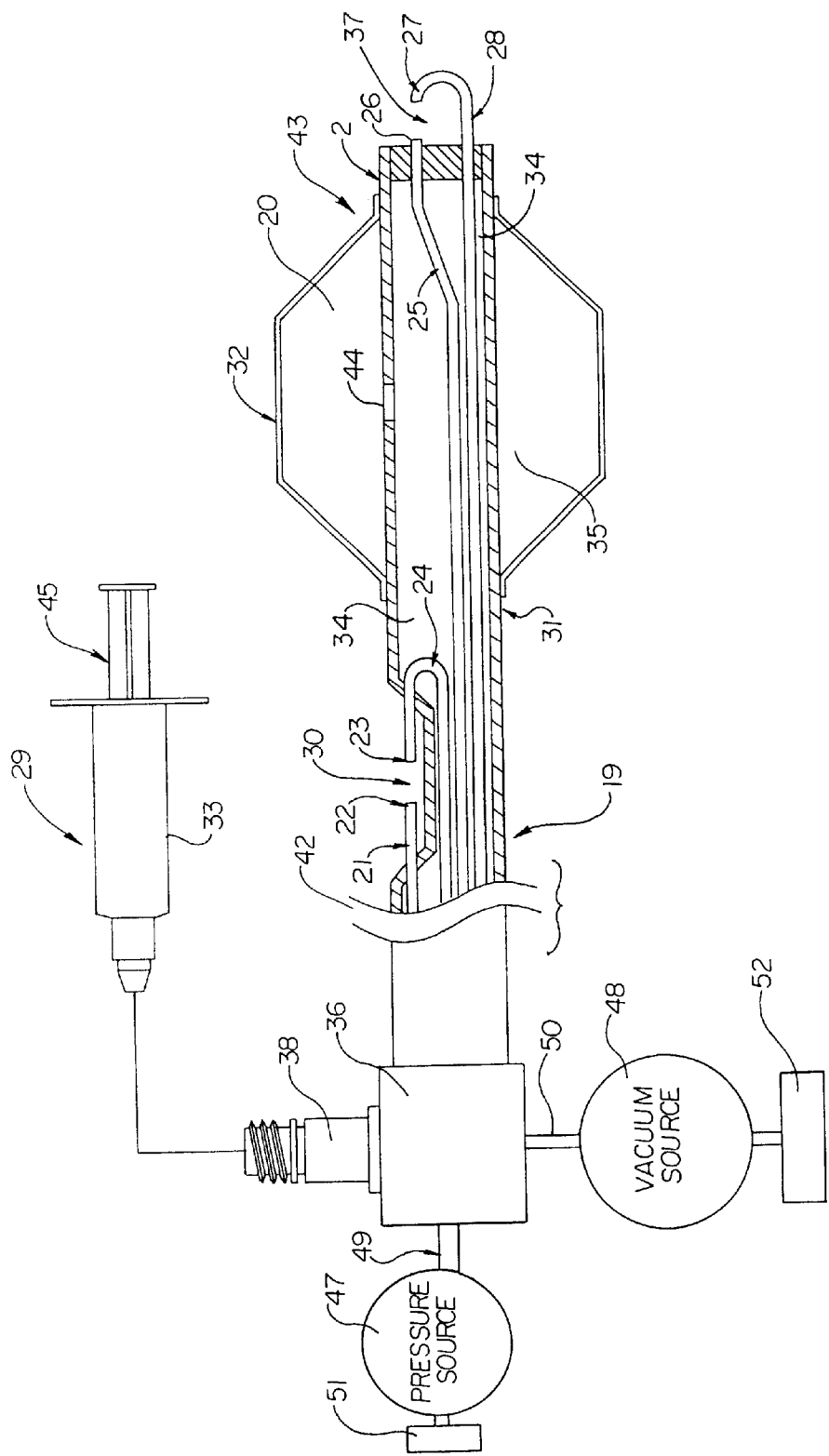
FIG. 5 is a partial cross-sectional view of the catheter system in accordance with an additional exemplary embodiment of the present invention.

FIG. 5 is a partial cross-sectional view of a catheter system in accordance with an additional embodiment of the present invention. Catheter system 19 includes a catheter 31 which may preferably be used for treating a blood vessel having an inner surface and one or more plaque deposits that include a core material.

Catheter 31 includes an elongate shaft 2 having proximal end 42 and distal end 43. In the particular embodiment of catheter 31, a balloon 20 comprising a balloon engagement surface 32 is disposed about a portion of elongate shaft 2. In a preferred embodiment, balloon 20 and balloon engagement surface 32 are adapted for engaging one or more plaque deposits, causing core material to extrude therefrom.

Elongate shaft 2 defines a first tubular member 24 having a first delivery port 23 disposed proximally of balloon 20. Elongate shaft 2 further defines a second tubular member 21 having a first collection port 22 disposed proximally venturi section 30.

Elongate shaft 2 defines a third tubular member 28 having a second delivery port 27 disposed distally of balloon 20. Elongate shaft 2 defines a fourth tubular member 25 having a second collection port 26 disposed proximally venturi section 37.

The second tubular member 21 and fourth tubular member 25 can be used to collect core material that has been extruded from a plaque deposit. The second tubular member 21 and fourth tubular member 25 can also be used to collect thrombus.

In the embodiment illustrated in FIG. 5, elongate shaft 2 further defines inflation lumen 34 and inflation port 44. Inflation lumen 34 and inflation port 44 are both in fluid communication with chamber 35 defined by balloon 20.

FIG. 5 further illustrates a hub 36 disposed about elongate shaft 2 proximate proximal end 42 thereof. In the embodiment of FIG. 5, hub 36 includes an inflation hub 38, fluid port 49, and return port 50. In FIG. 5, fluid source 29 is shown coupled to inflation hub 38. Fluid source 29 is preferably capable of introducing fluid into chamber 35 of balloon 20. In the embodiment of FIG. 5, fluid source 29 includes housing 33 defining a variable volume chamber that can be in fluid communication with inflation lumen 34 of elongate shaft 2. In this exemplary embodiment, fluid source 29 further includes a plunger 45 slidingly disposed within the variable volume chamber. When plunger 45 is depressed proximally, fluid is moved from fluid source 29 through inflation hub 38, hub 36, inflation lumen 34 and inflation port 44 into chamber 35 of balloon 20, causing the balloon to inflate. Conversely, when plunger 45 is pulled distally, fluid is drawn from chamber 35 of balloon 20 through inflation port 44, inflation lumen 34, hub 36 and inflation hub 38 back into the variable volume chamber of fluid source 29, causing the balloon to deflate. It is to be appreciated that the catheter system may include various fluid sources without deviating from the spirit and scope of the present invention. Examples of fluid sources that may be suitable in some applications include I.V. bags and peristaltic pumps.

In a preferred embodiment, balloon 20 has an inflated shape and a deflated shape. In FIG. 5, balloon 20 is shown in the inflated shape. Balloon 20 may be selectively inflated by introducing fluid from fluid source 29 into chamber 35 of balloon 20. Balloon 20 may be selectively deflated by drawing fluid from chamber 35 of balloon 20 back into fluid source 29.

To provide fluidic pressure to venturi section 30 and venturi section 37, first tubular member 24 and third tubular member 28 are in fluid communication with a fluid reservoir 51 and pressure source 47. In operation, pressure source 47 draws fluid from fluid reservoir 51 through pressure port 49 and hub 36 to first tubular member 24 and third tubular member 28. The fluid is then returned from second tubular member 21 and fourth tubular member 25 to an intake reservoir 52 through hub 36 and return port 50. In the exemplary embodiment shown in FIG. 5, an optional vacuum source 48 can be introduced between return port 50 and intake reservoir 52 to further aid in collecting plaque deposits from venturi section 30 and venturi section 37.

The elongate shaft 2 may be comprised of a single material, or a combination of materials, without deviating from the scope and spirit of the present invention. For example, elongate shaft 2 may include an inner tube. The inner tube can be comprised of polytetrafluoroethylene (PTFE). PTFE creates a smooth, low-friction surface for the passage of other devices through elongate shaft 2. Elongate shaft 2 may also include a support member wound or braided around the inner tube. The support member can be comprised of a plurality of filaments. The filaments may be comprised of stainless steel wire. Those with skill in the art will appreciate that other embodiments of a support member are possible without deviating from the spirit and scope of the present invention. For example, a support member may comprise a woven polymer fabric. By way of a second example, a support member may comprise polymer fibers wound in a braided pattern.

In a presently preferred embodiment, elongate shaft 2 comprises polyether block amide (PEBA). Polyether block amide is commercially available from Atochem Polymers of Birdsboro, Pa. under the trade name PEBAX. Also, elongate shaft 2 can be fabricated using an extrusion process. In this process, molten PEBA may be extruded onto the combined layers of an inner tube and a support member. When this process is utilized, the extruded material fills any interstitial spaces in the support member.

It is to be understood that other manufacturing processes can be used without departing from the spirit and scope of the present invention. Examples of materials that may be suitable in some applications include: polyethylene (PE), polypropylene (PP), polyvinylchloride (PVC), polyurethane, and polytetrafluoroethylene (PTFE).

Having thus described several embodiments of the present invention, those of skill in the art will readily appreciate that other embodiments may be made and used which fall within the scope of the claims attached hereto. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention.

What is claimed is:

1. A catheter for treating a blood vessel having an inner surface and one or more plaque deposits including a core material, comprising:

an elongate shaft having a proximal end and a distal end;

a first balloon attached to first portion of the elongate shaft for engaging one or more plaque deposits from the inner surface of the blood vessel and extracting the core material therefrom;

a second balloon attached to a second portion of the elongate shaft for engaging one or more plaque deposits from the inner surface of the blood vessel and extracting the core material therefrom; and a first venturi section disposed between the first balloon and the second balloon.

2. The catheter or claim 1, wherein the first venturi section comprises:

a first tubular member in fluid communication with a fluid source;

and a second tubular member in fluid communication with a fluid reservoir.

3. The catheter of claim 2, wherein the first tubular member includes a first delivery port for delivering a first fluid stream and the second tubular member includes a first fluid collection port configured such that it receives the first fluid stream.

4. The catheter of claim 2, wherein the first tubular member and the second tubular member comprise hypodermic tubing.

5. The catheter of claim 2, wherein the first tabular member includes a bent portion.

6. The catheter of claim 5, wherein the bent portion of the first tubular member comprises a generally J-shaped portion.

7. The catheter of claim 5, wherein the bent portion of the first tubular member comprises a generally portion terminating in a fluid delivery port.

8. The catheter of claim 2, wherein the first tubular member has an inner diameter that is generally smaller than the inner diameter of the second tubular member.

9. The catheter of claim 2, wherein the first tubular member has an inner diameter that is substantially similar to the inner diameter of the second tubular member.

10. A method for treating vulnerable plaque deposits within a blood vessel having an inner surface and one or more plaque deposits containing a core material, comprising the steps of:

providing a catheter with an elongate shaft having a proximal end and a distal end, a first balloon attached to a portion of the elongate shaft for engaging one or more plaque deposits and extracting the core material therefrom, a second balloon attached to a portion of the elongate shaft distal for engaging one or more plaque deposits and extracting core material therefrom, and a first venturi section disposed between the first and second balloons;

inserting a distal portion of the catheter into the lumen of a blood vessel;

positioning the first balloon proximate to, and the second balloon distal to, a plaque deposit;

inflating the balloons;

delivering a first stream of fluid to the first venturi section; and collecting the first stream of fluid.

11. A catheter for treating a blood vessel having an inner surface and one or more plaque deposits including a core material, comprising:

an elongate shaft having a proximal end and a distal end, wherein the elongate shaft may contain a fluid; fluid a first balloon and a second balloon disposed about a first portion and a second portion respectively of the elongate shaft for engaging the inner surface of the blood vessel adjacent one or more of the plaque deposits, wherein the first and second balloons may be inflated by forcing the fluid into the elongate shaft from its proximal end; and a venturi section disposed at a third portion of the elongate shaft for aspirating core material from one or more of the plaque deposits.

12. The catheter of claim 11, wherein the elongate shaft includes a first inflation port for inflating the first balloon with the fluid, and a second inflation port for inflating the second balloon with the fluid.

* * * * *

UNITED STATES PATENT AND TRADEMARK OFFICE
CERTIFICATE OF CORRECTION

PATENT NO. : 6,790,196 B2
DATED : September 14, 2004
INVENTOR(S) : Jaydeep Y. Kokate and Eric M. DoBrava It is certified that error appears in the above-identified patent and that said Letters Patent is hereby corrected as shown below:

Title page,
Item [75], Inventor, Jaydeep Y. Kokate, please delete "US" and insert -- India -- therefor;

Column 5,
Line 20, after "to" please insert -- a --;
Line 31, please delete "or" and insert -- of -- therefor;
Line 39, after "stream" please insert -- ; --;
Line 46, please delete "tabular" and insert -- tubular -- therefor;
Line 51, after "generally" please insert -- J-shaped --;

Column 6,
Line 35, please delete second occurrence of "fluid".

Signed and Sealed this

Fourth Day of January, 2005

JON W. DUDAS
*Director of the United States Patent and Trademark Office*